US006810743B2

(12) United States Patent
Madaras et al.

(10) Patent No.: US 6,810,743 B2
(45) Date of Patent: Nov. 2, 2004

(54) NON-DESTRUCTIVE EVALUATION OF WIRE INSULATION AND COATINGS

(75) Inventors: Eric I. Madaras, Yorktown, VA (US); Robert F. Anastasi, Hampton, VA (US)

(73) Assignee: The United States of America as represented by the Administrator of the National Aeronautics and Space Adminstration, Washington, DC (US)

( * ) Notice: Subject to any disclaimer, the term of this patent is extended or adjusted under 35 U.S.C. 154(b) by 0 days.

(21) Appl. No.: 10/212,563

(22) Filed: Aug. 1, 2002

(65) Prior Publication Data

US 2004/0182160 A9 Sep. 23, 2004

Related U.S. Application Data

(60) Provisional application No. 60/396,498, filed on Jul. 17, 2002, provisional application No. 60/433,622, filed on Apr. 24, 2002, and provisional application No. 60/311,967, filed on Aug. 1, 2002.

(51) Int. Cl.[7] .............................................. G01N 29/08
(52) U.S. Cl. ......................................... 73/598; 73/600
(58) Field of Search ........................ 73/597, 598, 599, 73/600, 643

(56) References Cited

U.S. PATENT DOCUMENTS

| | | | |
|---|---|---|---|
| 3,987,674 A | * | 10/1976 | Baumoel ..................... 73/597 |
| 4,380,931 A | | 4/1983 | Frost et al. |
| 4,593,244 A | | 6/1986 | Summers et al. |
| 4,659,991 A | | 4/1987 | Weischedel |
| 4,929,897 A | | 5/1990 | Van Der Walt |
| 4,979,125 A | | 12/1990 | Kwun et al. |
| 5,115,673 A | | 5/1992 | Kline et al. |
| 5,390,544 A | | 2/1995 | Madras |
| 5,456,113 A | | 10/1995 | Kwun et al. |
| 5,457,994 A | | 10/1995 | Kwun et al. |
| 5,804,727 A | * | 9/1998 | Lu et al. ..................... 73/597 |
| 6,450,036 B1 | * | 9/2002 | Ashida et al. ............... 73/597 |

FOREIGN PATENT DOCUMENTS

WO WO99/27360 * 6/1999

OTHER PUBLICATIONS

Wolfgang Sachse and Yih–Hsing Pao, "On the Determination of Phase and Group Velocities of Dispersive Waves in Solids," American Institute of Physics, Cornell University (Ithaca), vol. 8 (No. 49), p. 4320–4327, Aug. 1978.

T.R. Meeker and A.H. Meitzler, "Guided Wave Propagation in Elongated Cylinders and Plates," Physical Acoustics, Academic Press (Murray Hill), vol. 1 (No. A), p. 111–167, (Aug. 1, 1964).

R.N. Thurston, "Elastic Waves in Rods and Clad Rods," Acoustical Society of America, Bell Telephone Laboratories (Holmdel), vol. 1 (No. 64), p. 1–37, (7/78).

(List continued on next page.)

Primary Examiner—John E. Chapman
(74) Attorney, Agent, or Firm—Robin W. Edwards

(57) ABSTRACT

The present invention uses the generation and detection of acoustic guided waves to evaluate the condition of the insulation on electrical wiring. Low order axisymmetric and flexural acoustic modes are generated in the insulated wire and travel partially in the center conductor and partially in the outer insulation. The stiffness of the insulation and the insulation's condition affect the overall wave speed and amplitude of the guided wave. Analysis of the received signal provides information about the age or useful life of the wire insulation. In accordance with the present invention, signal transmission occurs at one location on the electrical wire to be evaluated, and detection occurs at one or more locations along the electrical wire. Additional receivers can be used to improve measurement accuracy. Either the transmission transducer or one or more receiver transducers may be angled at other than 90 degrees to the wire. Generation of the guided waves can be accomplished by imparting a pressure pulse on the wire. Alternative embodiments include generation via a laser, such as a Q-switched laser or a laser diode.

60 Claims, 16 Drawing Sheets

OTHER PUBLICATIONS

H.D. McNiven, J.L. Sackman, and A.H. Shah, "Dispersion of Axially Symmetric Waves in Composite, Elastic Roads," The Journal of the Acoustical Society of America, 1st ed., University of California (Berkeley), vol. 35 (No. 10), p. 1602–1609, (Oct. 1963).

H. Norman Abramson, "Flexural Waves in Elastic Beams of Circular Cross Section," The Journal of the Acoustical Society of America, Southwest Research Institute (San Antonio), vol. 29 (No. 1), p. 42–46, (Jan. 1957).

E.I. Madaras, T. Kohl, and W.P. Rogers, "Material Property Characterization and Pulse Propagation in Thin Drawn Wire Waveguides," Ultrasonics Symposium, NASA Langley Research Center & Univ. of Colorado (Hampton), p. 957–962, 1992.

Eric I. Madaras, Thomas W. Kohl, and Wayne P. Rogers, "Measurement and Modeling of Dispersive Pulse Propagation in Drawn Wire Waveguides," Acoustical Society of America, 1st ed., NASA Langley Research Center and Univ. of Colorado (Hampton), p. 252–261, (1/95).

Cynthia Furse and Randy Haupt, "Down to the Wire," IEEE Spectrum, Utah State University, p. 34–39, (Feb. 2001).

A.M. Bruning and F.J. Campbell, "Aging in the Wire Insulation Under Multifactor Stress," IEEE Transactions on Electrical Insulation, Lectromechanical Design Company and U.S. Naval Research Lab. (Herndon), vol. 28 (No. 5), p. 729–754, (Oct. 1993).

Robert F. Anastasi and Eric I Madaras, "Investigating the Use of Ultrasonic Guided Waves for Aging Wire Insulation Assessment," SPIE's 7th Annual International Symposium on NDE for Helath Monitoring and Diagnostics, U.S. Army Research Lab and NASA LaRC, (San Diego) (Mar. 17, 2002).

R.F. Anastasi and E.I. Madaras, "Pulse Compression Techniques for Laser Generated Ultrasound," IEEE International Ultrasonic Symposium, U.S. Army and NASA LaRC, (Lake Tahoe) (Oct. 17, 1999).

Eric I. Madaras and Robert F. Anastasi, "Pseudo–Random Modulation of a Laser Diode for Generating Ultrasonic Longitudinal Waves," 26th Annual Review of Progress in QNDE, U.S. Army Research Lab and NASA LaRC (Montreal), (Jul. 25, 1999).

Eric I. Madaras and Robert F. Anastasi, "Investigating the Use of Ultrasound for Evaluating Aging Wiring Insulation," 5th Joint NASA/FAA/DoD Conference on Aging Aircraft, NASA LaRC and U.S. Army Research Lab (Orlando), (Sep. 10, 2001).

* cited by examiner

◆ F1: First Flexural Mode
■ F2: Second Flexural Mode
▲ S0: Lowest Order Axisymmetric Mode
— Cosine Squared

NON-DESTRUCTIVE EVALUATION OF WIRE INSULATION AND COATINGS

CLAIM OF BENEFIT OF PROVISIONAL APPLICATION

The invention described herein was made by employees of the United States Government and may be used by or for the Government for governmental purposes without the payment of any royalties thereon or therefor.

ORIGIN OF INVENTION

Pursuant to 35 U.S.C. §119, the benefit of priority from provisional application Ser. No. 60/311,967, entitled "Method and Apparatus for Evaluating Insulated Wire", with a filing date of Aug. 1, 2001, application Ser. No. 60/433, 622, entitled "Method and Apparatus for Evaluating Insulated Wire", with a filing date of Apr. 24, 2002, and application Ser. No. 60/396,498, entitled "Method and Apparatus for Evaluating Insulated Wire", with a filing date of Jul. 17, 2002, is claimed for this non-provisional application.

BACKGROUND OF THE INVENTION

1. Field of the Invention

The present invention relates broadly to the field of nondestructive examination and more specifically to the nondestructive examination of wiring. Even more specifically, the present invention relates to the nondestructive examination of wire insulation and coatings.

2. Description of the Related Art

Electrical wiring is critical to the operation of most modern day equipment and, in its operation, is subjected to heat, cold, moisture, vibrations, tension and other environmental conditions which eventually may cause the wire insulation and even the wire conductor to fail. In most cases, these environmental and operational conditions are modest and wiring is used for years, but in some cases these conditions are extreme and cause the insulation to become brittle and crack. The cracks expose the underlying wire conductor and become a potential source for short circuits and fire.

There are few available methods to evaluate the condition of the insulation on electrical wiring. Typical wire inspections are done visually and often after the fact, in response to an instrument or system failure. A visual inspection often fails to detect many cracks and flaws because the cracks and flaws are not visible or are located in spaces that are difficult to see. Furthermore, a visual inspection offers little quantitative information about the condition of the wire insulation. Some techniques require a section of wire to be removed for laboratory testing. These techniques are undesirable due to their destructive nature. There are also techniques that involve application of voltage to the wire to detect current leakage. The current leakage is indicative of an insulation failure, such as cracking, but does not provide predictive information on the state of the insulation. Some of the voltage application techniques are conducted in air, while others imbed the wires in a conductive medium. Additionally, some involve high voltage while others have been designed to detect leakage at low voltages.

Meeker, T. R., and Meitzler, A. H., "Guided Wave Propagation in Elongated Cylinders and Plates," *Physical Acoustics—Principles and Methods*, edited by W. P. Mason, Academic Press, N.Y., Vol. 1, Part A., 1964, pp.111–167; Thurston, R. N., *J. Acoust. Soc. Am.*, 64, 1, 1–37, (1978); McNiven, H. D., Sackman, J. L., and Shah, A. H., *J. Acoust. Soc. Am.*, 35, 10,1602–1609, (1963), and Abramson, H. N., *J. Acoust. Soc. Am.*, 29, 1, 42–46, (1957) examined acoustic guided wave propagation in cylindrical geometry. Madaras, E. I., and Anastasi, R. F., "Pseudo-Random Modulation of a Laser Diode for Generation Ultrasonic Longitudinal Waves," 26 *Annual Review of Progress in Qualitative Nondestructive Evaluation*, Montreal, Quebec, Canada, July 1999, and Anastasi, R. F. and Madaras, E. I., "Pulse Compression Techniques for Laser Generated Ultrasound," *IEEE International Ultrasonics Symposium*-1999, edited by S. C. Schneider and B. R. McAvoy, IEEE Ultrasonics, Ferroelectronics, and Frequency Control Society, 1999, both incorporated herein by reference, examined ultrasonic guided waves for characterization of wire.

There are numerous methods for wire nondestructive examination that involve investigation of the conductor. One method is Time Domain Reflectometry (TDR) and another is Standing Wave Reflectometry (SWR). These methods and related variants are sensitive to the conductor but are only mildly affected by the condition of the insulation. Furthermore, these methods only detect insulation failure.

U.S. Pat. No. 4,380,931 (Frost, et al.), utilizing a plurality of noncontacting ultrasonic transducers in cooperation with a magnetic field, is applicable only to conductive wires, and more specifically only to solid cylindrically shaped objects, not stranded wires with insulation. Furthermore, only torsional waves are produced in a solid conductor. U.S. Pat. No. 5,457,994 (Kwun et al.) utilizes the magnetoresistive effect to generate and detect acoustic waves to measure the condition of conducting wires, but does not detect the surrounding materials' condition. U.S. Pat. No. 4,593,244 (Summers et al.) is limited to measuring the thickness of conductive coatings that are on ferromagnetic substrates. In general, electrical wires that are usually of interest do not utilize a conductive coating and, in addition, the thickness of a wire coating is, in general, not the only concern that faces most electrical wire users.

U.S. Pat. Nos. 4,659,991 (Weischedel), 4,929,897 (Van Der Walt), 4,979,125 (Kwun et al.), and 5,456,113 (Kwun et al.) teach methods that are applicable only to ferromagnetic materials. None of the aforementioned patents teach nondestructive examination of wire insulation. U.S. Pat. No. 4,659,991 (Weischedel), detects shape changes in a cable and uses magnetic fields to sense the shape changes, but is not relevant to wire insulation. U.S. Pat. No. 4,929,897 (Van Der Walt), also detects shape changes in a cable and also uses magnetic fields from a different sensor geometry than Weishedel to sense the shape changes, and again is not relevant to wire insulation. U.S. Pat. No. 4,979,125 (Kwun et al.) tests a cable, rope or metal strand (which are not insulated) by first striking the cable with an impulse such as a hammer or electromagnetically driven plunger, and then detecting the resulting vibrations with a magnetic sensor. U.S. Pat. No. 5,456,113 (Kwun et al.) tests ferromagnetic cables and ropes (which are not insulated) by inducing and detecting acoustic/ultrasonic waves by a magnetorestrictive means.

It is therefore an object of the present invention to provide a nondestructive method and apparatus for evaluating the condition, both prior to and subsequent to failure, of the insulation on electrical wiring.

It is another object of the present invention to provide a nondestructive method and apparatus for evaluating the condition of wire insulation quantitatively, giving the user information on the expected safe remaining life of the wire.

It is another object of the present invention to provide a nondestructive method and apparatus for evaluating the condition of either ferromagnetic or nonferromagnetic insulation on electrical wiring.

It is yet another object of the present invention to provide a nondestructive method and apparatus to utilize ultrasonic wave generation to evaluate the condition of electrical wire insulation.

It is yet another object of the present invention to provide a nondestructive method and apparatus for evaluating the condition of electrical wire conductors.

It is yet another object of the present invention to provide a nondestructive method and apparatus for evaluating the condition of wire coatings.

Still other objects and advantages of the present invention will in part be obvious and will in part be apparent from the specification.

SUMMARY OF THE INVENTION

The present invention uses the generation and detection of acoustic guided waves to evaluate the condition of the insulation on electrical wiring. Low order axisymmetric and flexural acoustic modes are generated in the insulated wire. These modes travel partially in the center conductor and partially in the outer insulation. The stiffness of the insulation and the insulation's condition affect the overall wave speed and amplitude of the guided wave. Thus, the measurement of wave speed will in part be a measurement of material stiffness and, in part, be a measurement of insulation condition. Analysis of the received signal provides information about the age or useful life of the wire insulation.

Although there are other, higher order modes that are generated, the two lowest order modes mentioned are generally the easiest to excite. The flexural mode is one of the largest generated. Although the axisymmetric mode is generally small, it is easy to measure, and thus desirable to use. Little or no axisymmetric mode is generated with the laser generation method, to be discussed later, most likely reflecting the small area of generation in contrast to the larger area of a transducer. The particular mode to be utilized is determined based on the ease of generation, low attenuation, and sensitivity to the damage being tested for. Some testing of a baseline sample will generally be needed to determine which mode to utilize.

The wave speed and attenuation of the waves are measured and provide information about the physical condition of the insulation. The speed measurement is related to the stiffness and density of the material components. The attenuation measurement is related to the structure and microstructure of the component materials, such as microcracks in the insulation. In general, wire insulations are of a polymer base and have much lower stiffness characteristics than the center conductor, which is usually copper or aluminum. Because copper and aluminum have a much higher wave speed than polymers, the effect of wrapping insulation on a cylindrical shaped conductor will be to lower the wave speed of the guided wave. As the insulation is aged, it will loose its plasticity and harden, which will lead to cracks, exposing the center conductor, which could lead to electrical shorting. As the insulation hardens, the coating material will stiffen, which will cause the wave speed to be greater. The frequency content and amplitude information provide an indication of the insulation's condition, such as chaffing, cuts, nicks, cracks and flaws. Each of these conditions will attenuate the signal. Both flaws and degradation will affect the signals. For example, a nick in the insulation changes the frequency content of the signal, whereas degradation alters the signal speed and attenuation. The present invention is applicable to any conductor material, with the details of the wave motion depending on the relative constituents.

In accordance with the present invention, signal transmission occurs at one location on the electrical wire to be evaluated, and detection occurs at one or more locations along the electrical wire. The number and position of detection locations depends on the user's preference. In one embodiment, transmission and detection occurs at one location, which is especially effective for evaluating the termination points of wire, such as at connectors, as well as for detecting signals reflected from flaws. For connectors, one transducer can be used to transmit the signal to the connector and detect the reflected signal. The transducer would be positioned as close as possible to the connector. Evaluation can consist of viewing the waves or estimating the wave velocity based on the distance of the transducer from the connector. With a flaw, the existence of the flaw would produce a signal anomaly.

In another embodiment, detection occurs at one or more locations separate from the transmitting location. This configuration generally has good signal to noise. The positioning of the transducers is dependent upon the anticipated region of criticality. Often certain areas are more suspect than others and should be inspected with more detail and frequency. General areas could be spot checked if desired. Two simultaneous measurements can be taken to generate both attenuation and speed values. If the distances between any two pairs of transmit or detect transducers are not equal, then the difference between the time of the received signals divided into the differences in transducer spacing will give the velocity of the ultrasonic wave. Additional receivers can be used to improve measurement accuracy.

In further alternative embodiments, either the transmitter transducer or one or more receiver transducers may be angled at other than 90 degrees to the wire.

Generation of the guided waves can be accomplished by imparting a pressure pulse on the wire. Alternative embodiments include generation via a laser, such as a Q-switched laser or a laser diode.

The detected signal can be further processed to extract the material properties of interest with respect to the wire insulation. One method of processing is to apply the generation and detection to wires exhibiting a range of conditions, both acceptable and unacceptable, to produce a look-up table of velocity or attenuation properties for that specific wire type that could then classify an unknown wire specimen. Another method is to apply modeling. By setting up the differential equations for the particle motions and stresses and strains, and matching the boundary conditions at the interface of the conductor to insulation and the insulation to air, an ultrasonic propagation model for a wire covered by insulation can be developed. A further general description of such modeling can be found in the earlier references to Meeker, T. R., and Meitzler, A. H.,; Thurston, R. N.,; McNiven, H. D., Sackman, J. L., and Shah, A. H.,; and Abramson, H. N. Then, using known properties for the conductor and the dimensions of the wire, the properties of the insulation can be inferred utilizing mathematical techniques via a computer. Examples of commercially available software include Disperse, as well as general software in commercial packages such as Numerical Methods in C, Mathematica, MatLab, and IDL. In a similar method, finite element method or finite difference modeling software can be used to accomplish the same result, although generally more expensive.

The present invention provides the capability to measure velocities, frequencies, and magnitudes. The system is adapted to measure characteristics that are relevant to the flaw/degradation being tested for. For example, the signal's frequency content would be significantly changed and the attenuation would be worse for severe chafing.

In addition to the evaluation of insulation, the present invention can also be used for evaluating coatings, as well as the conductor itself. It can also be used to evaluate stranded wire. The system is adapted, frequency for example, to measure the particular constituent condition. The invention can be used for any layered media, including cylindrical or rectangularly shaped structures, and including media that is not conductive. The stiffness of various layers would determine the ultimate efficacy of any testing. At the lowest frequencies, it would test the whole structure, but at higher frequencies, it would tend to test the layers with the lowest stiffness.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
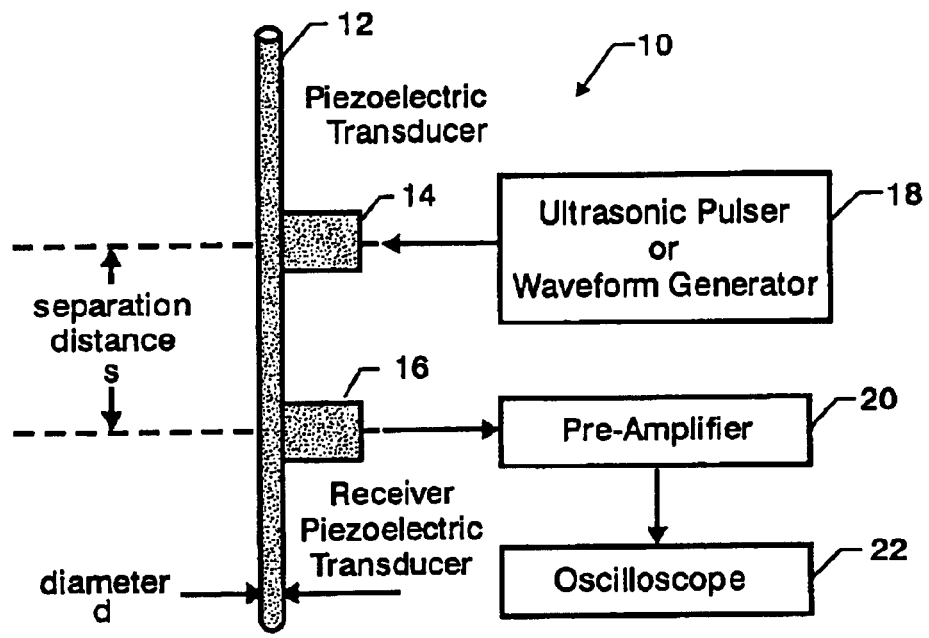
FIG. 1 shows a schematic of an embodiment of the present invention having a single transmitter transducer and a separate single receiver transducer.

Referring now to the drawings, and more particularly to FIG. 1, an embodiment of the present invention is shown and referenced generally by numeral 10. In describing the embodiments of the present invention, like numerals used in the various figures refer to like features of the invention. In the embodiment illustrated, signal generation occurs at a single location along wire 12 and detection occurs at a single separate location along wire 12. A piezoelectric transducer 14 generates the guided waves in combination with an ultrasonic pulser or waveform generator 18. Other transducers are also acceptable, but piezoelectric transducers are commonly used and function well for this purpose. Use of the ultrasonic pulser or waveform generator 18 imparts a pressure pulse on the wire 12. The use of an ultrasonic pulser will generate many frequencies at once, whereas a waveform generator would be used to generate a more specific set of frequencies. The pressure pulse application will set up numerous flexural and axisymmetric waves that will transmit through the length of wire 12 in both directions. These modes travel partially in the center conductor and partially in the outer insulation.

Figure 2:
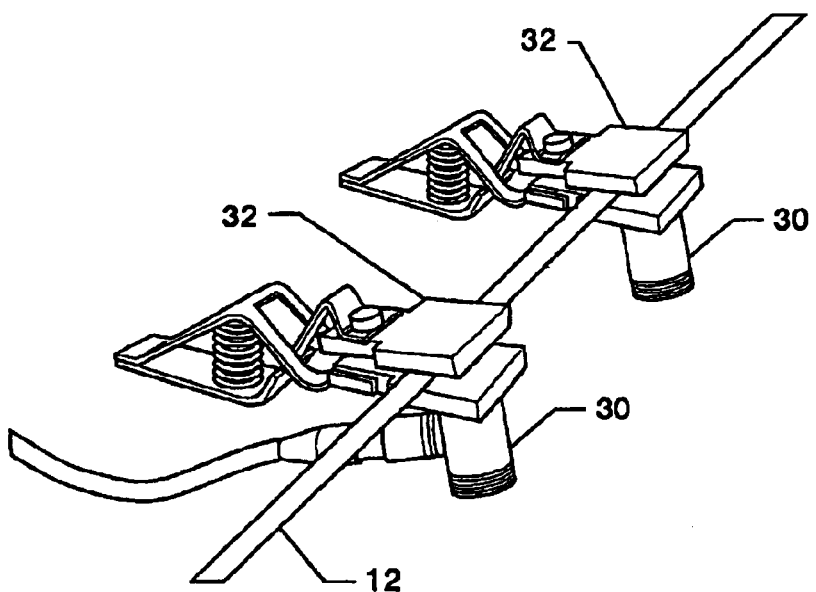
FIG. 2 shows transducers clipped to a wire.

Use of low frequency, wide band transducers, as shown in FIG. 2, clamped onto the wire allow for reliable, repeatable coupling to overcome transducer coupling. The transducers 30 are mounted in holders 32 that can be clamped to the wire 12. The holder 32 holds the wire across the center of the transducer 30 face. Contact between the transducer 30 and the wire 12 is critical to producing a repeatable measurement. The clamping allows for control of where the transducer touches the wire so that a reliable signal can be reproduced and to provide a solid contact for both generation and detection.

The frequency range of interest for the transducers 30 will depend in part on the flaws being tested for and the general dimensions of the wire 12. An example of a suitable transducer is a ⅜" acoustic emission transducer, which is small, sensitive to low frequencies (~50 KHz), and wide band (up to ~2 MHz). Examples of suitable pulsers are Panametrics and Metrotek pulsers. An example of a suitable waveform generator is a LeCroy arbitrary waveform generator. One example of a suitable transmitter transducer 14 and receiver transducer 16 is a broadband acoustic emission piezoelectric transducer that operates in the 200–300 kHz range. These piezoelectric transducers are capable of generating a signal that transmits a fairly long distance without much attenuation. The signals that are created in the wire would also be in the 200–300 kHz range with lower frequency signals traveling better (with less attenuation) than higher frequency signals. The shape and type of wire 12 under evaluation determines what frequencies are generated. In general, the larger the wire, the lower the frequencies that are used. The signal is detected by receiver transducer 16 and amplified by pre-amplifier 20 prior to viewing on oscilloscope 22.

In its basic geometry, the insulated wire may be considered a cylindrical wave-guide or perhaps more descriptively, a clad rod, where the wire conductor is the core and the insulation is the cladding. In general, many acoustic waves will propagate in an isotropic cylinder. The lowest mode of vibration is the axisymmetric mode, which can be divided into axial-radial and torsional modes. The next order of vibration is the flexural mode, and higher modes are screw modes. The lowest branch of the axial-radial mode extends to zero frequency where the limiting phase velocity is called the bar velocity. In the low frequency regime this mode is nearly non-dispersive. As frequency increases the phase velocity drops to a value slightly below the Raleigh velocity and then approaches the Rayleigh velocity from below at higher frequencies.

Figure 3:
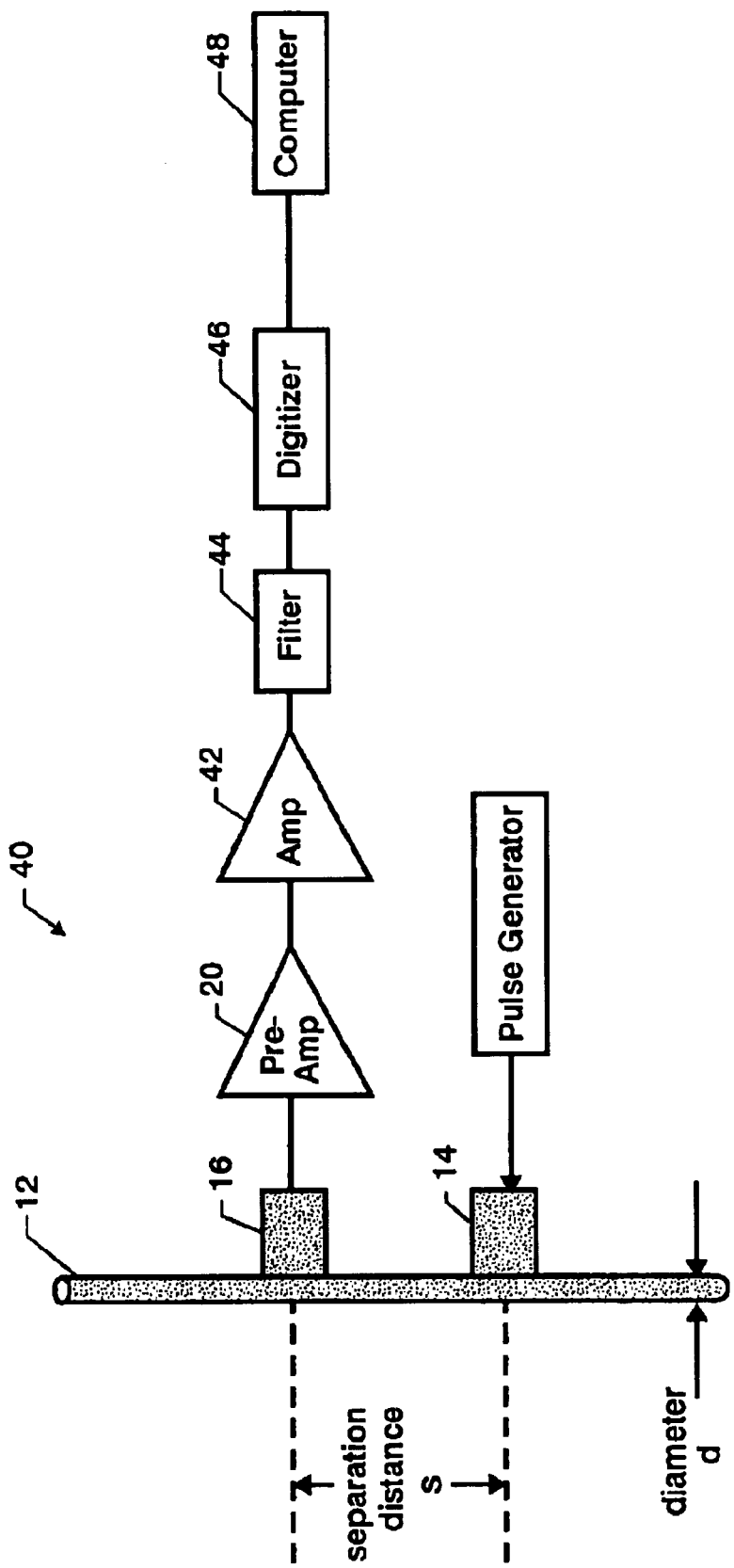
FIG. 3 shows a schematic of an embodiment utilizing transducers and incorporating pre-amplification, filtering and automation via digitizer and computer.

Another embodiment, shown in FIG. 3 and referenced generally by numeral 40, incorporates an additional amplifier 42, filters 44, digitizer 46 and computer 48. The signal is detected by receiver transducer 16, amplified by pre-amplifier 20 and amplifier 42 and filtered 44 to capture the acoustic wave or waves of interest. Examples of suitable pre-amps 20 are Panametrics (20–2000 KHz, with 40 or 60 dB of gain) or Digitial Wave (40–4000 KHz, with 30 dB). Examples of suitable amplifiers are Panameterics 5052 or Digital Wave's filter/amplifier which controls the frequency with high pass and low pass filters and with gain from 0 to 42 dB. The detected signal can then be digitized 46 and passed to computer 48 for processing. Pre-amplification is often needed for signal amplification. Filtering is helpful when suppression of higher modes is desired. Automation of the system requires the digitizer 46 and computer 48. The ultrasonic signals from different points on the wire can then be compared via analytic methods to measure the phase velocity and/or signal loss from the different modes. Suitable analytical methods include comparison to a preexisting look-up table of velocity or attenuation properties for the specific wire type, utilization of an ultrasonic propagation model, and finite element or finite difference modeling.

Figure 4A:
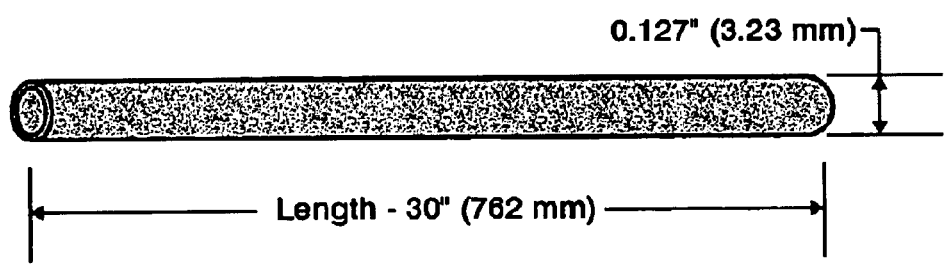
FIGS. 4A–4B show bare aluminum rod and polymer-coated aluminum rod test articles.
Figure 4B:
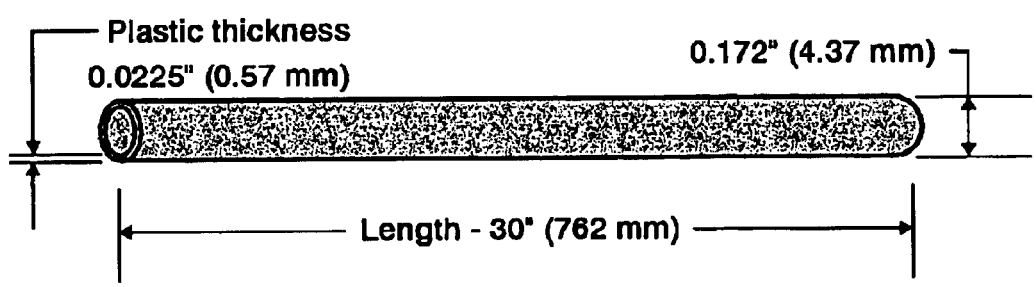

In one experimental example, referring to FIGS. 4A and 4B, the test articles consisted of a bare solid aluminum rod, as shown in FIG. 4A, and a solid aluminum rod having a polymer coating, as shown in FIG. 4B. The bare aluminum rod, simulating a wire conductor, had a 3.23 mm (0.127 in.) diameter. The polymer coating, simulating the insulation, had a thickness of 0.57 mm (0.0225 in.), resulting in an overall diameter of 4.37 mm (0.172 in.). The length of each rod was 762 mm (approximately 30 in.) The coating was thermoplastic heat-shrink Polyolefin. TABLE I shows the properties of the conductor and insulator. The experimental set-up shown in FIG. 1 was utilized.

TABLE I

| Properties* | Aluminum | Thermoplastic |
|---|---|---|
| Long. Velocity (m/s) | 6320 | 1868+ |
| Shear. Velocity (m/s) | 3130 | — |
| Bar Velocity (m/s) | 5119 | — |
| Density (gm/cm³) | 2.700 | 0.971 |

TABLE I-continued

| Properties* | Aluminum | Thermoplastic |
|---|---|---|
| Poisson's Ration | 0.338 | 0.458 |
| Young's Modulus (Gpa) | 70.76 | 1.2 |

*published values
+measured value

Figure 5:
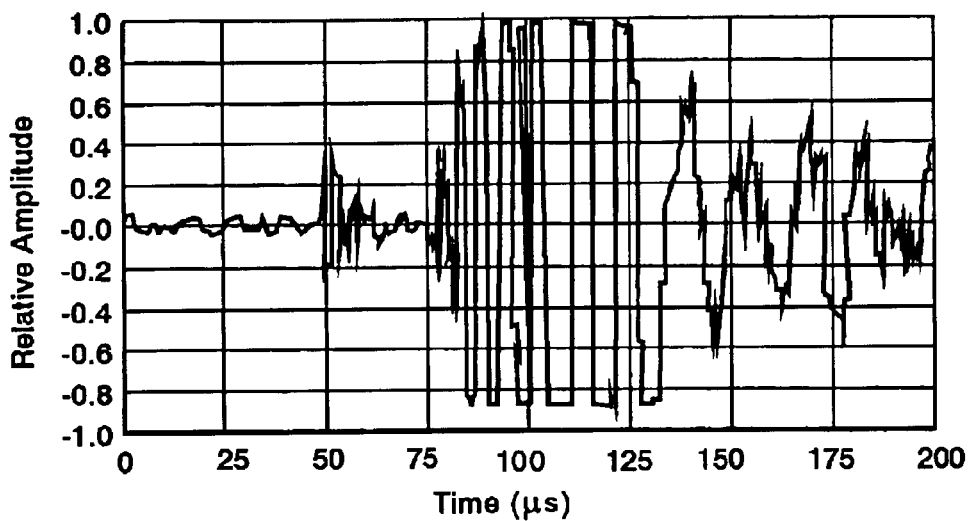
FIG. 5 illustrates a typical ultrasonic signal in the bare aluminum rod of FIG. 4A.
Figure 6:
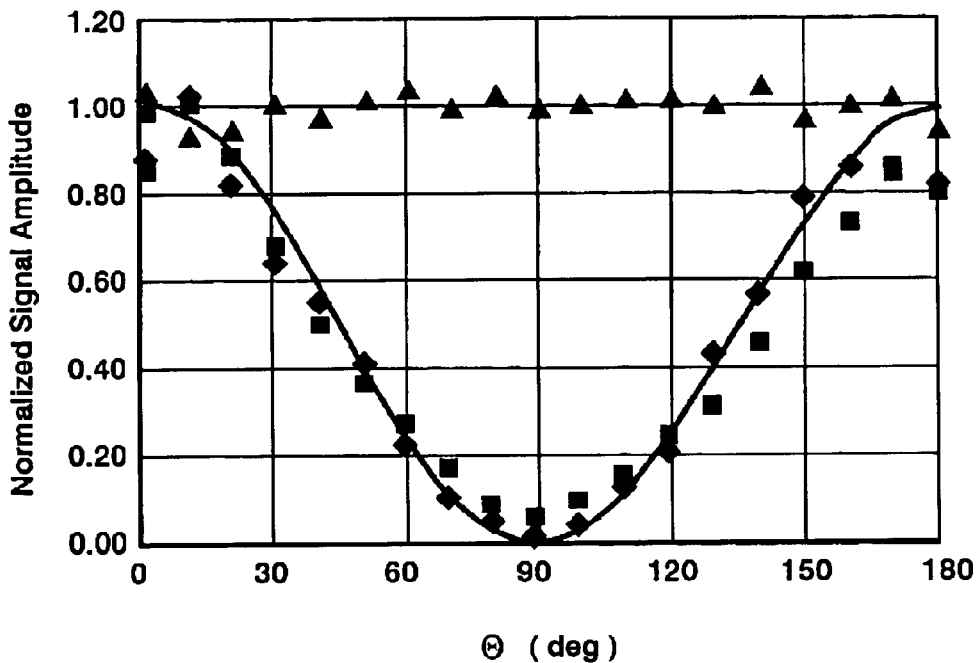
FIG. 6 illustrates axisymmetric and flexural mode amplitudes as a variation of detection angle.

Piezoelectric transmitter transducer 14 and piezoelectric receiver transducer 16 were separated by between approximately 3 to 30 cm, although other distances could be used. The transducers 14 and 16 each had a frequency range of 50 kHz to 1.5 MHz and were mechanically clipped to the test article, as shown in FIG. 2. The frequencies were chosen by the naturally generated frequencies that the wire tended to generate. A typical ultrasonic signal in the bare aluminum rod is shown in FIG. 5. The smaller amplitude wave at about 50 μs is the first axisymmetric wave mode and the larger amplitude wave initiating at about 75 μs is the first flexural mode wave. The amplitude difference between the axisymmetric and flexural wave modes is consistent with the geometry of the ultrasonic generation. Since the transmitter transducer 14 is located on the side of the rod, a larger amplitude bending force is applied to the rod, and thus a larger amplitude flexural mode is generated. To further investigate, the signal was examined as a function of rotational angle between the transmitting and receiving transducers. The transmitter transducer 14 was held stationary while the receiver transducer 16 was rotated around the aluminum rod in increments of 10 degrees. A plot of the resulting axisymmetric and flexural mode amplitudes is shown in FIG. 6. The axisymmetric mode amplitude is constant while the flexural mode amplitude follows a cosine-squared shape with a minimum at 90 degrees. Signals similar to those shown in FIG. 5 were observed when the distance between the transmitter transducer 14 and receiver transducer 16 was varied. The resulting signals, as a function of distance, demonstrate that the frequency content of the axisymmetric mode remains constant while the frequency content of the flexural mode varies and contains higher order modes. These higher order modes were evident in the signal as small changes or variation in the sinusoidal shape of the wave, and changed as the distance between the transducers was varied.

The phase velocity of the axisymmetric mode was determined by taking a series of measurements of a constant phase point as a function of transducer separation. Because the axisymmetric mode is faster than the flexural mode and arrives first, it is easy to isolate and measure. The separation distance of the two transducers varied from 50 mm to 250 mm, over which 10 to 12 measurements were taken. The phase point in time was plotted against the distance and a linear curve fit was applied to the data. The slope of the linear fit was the measure of the phase velocity. The phase velocity of the bare rod and the polymer coated aluminum rod were 5128 m/s and 4663 m/s, respectively. This phase velocity measurement in the bare aluminum rod is consistent with a calculated bar velocity of 5119 m/s. The measured changes in phase velocity between the bare and coated aluminum rod demonstrate the effect of the coating. This example illustrates the sensitivity of the lowest order axisymmetric mode to stiffness changes in the wire insulation. At the lowest frequencies of the flexural mode, there is less effect of the insulating material/coating on the wave speed. The sensitivity is not as great as in the low frequency axisymmetric mode.

Figure 7:
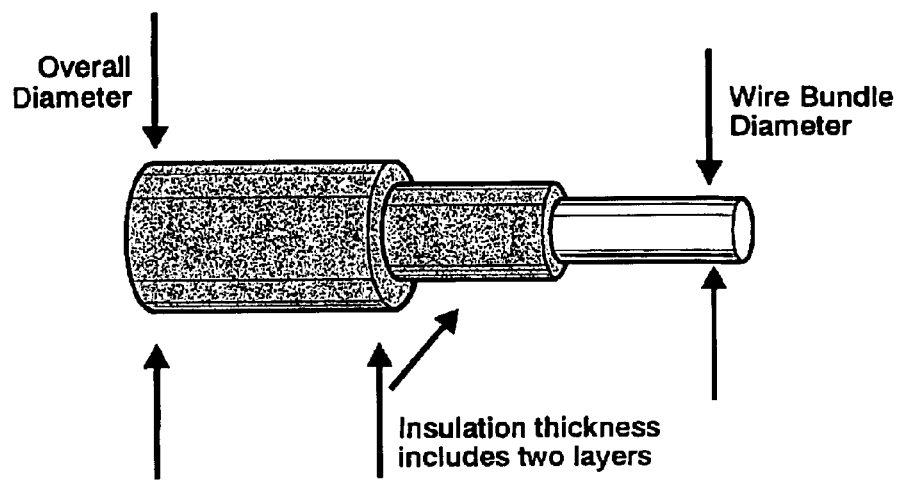
FIG. 7 shows a wire test article.

In a further experimental example, 12, 16 and 20 gauge Tefzel® coated MIL-W-22759/34 wire samples were heat-damaged. FIG. 7 shows the wire test article and TABLE II shows the diameter, strand number, and strand gauge as a

TABLE II

Figure 8:
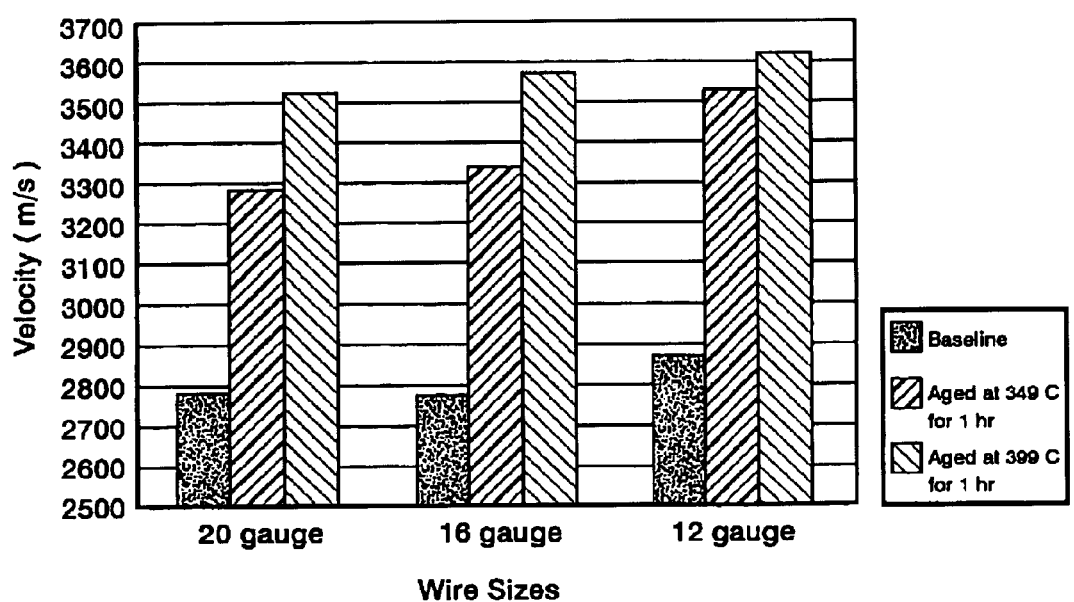
FIG. 8 shows experimental results for MIL-W-22759/34 wire.

|  | Gauge | | |
| --- | --- | --- | --- |
|  | 12 | 16 | 20 |
| Overall Dia. (mm) | 2.78 | 1.90 | 1.51 |
| Wire Bundle Dia. (mm) | 2.05 | 1.29 | 0.81 |
| Insulation Thk. (mm) | 0.365 | 0.305 | 0.35 |
| Wire strands per Bundle | 37 | 19 | 19 |
| Wire Strand Gauge | 28 | 29 | 32 | function of wire gauge. Three samples of each gauge wire were cut to a length of approximately 60 cm. One sample of each gauge was used for a baseline measurement, one sample of each gauge was heated in an oven at 349° C. for one hour, and one sample of each gauge was heated in an oven at 399° C. for one hour. The insulation on the baseline sample was smooth, flexible, and off-white in color. The samples that were heat damaged at 349° C. remained smooth and flexible but the color changed to gray. The samples heat damaged at 399° C. became brittle, cracked, and the color approached black. The phase velocity in each of these samples was measured following the same procedures described in the earlier experimental example and the results are shown in FIG. 8. As shown, the axisymmetric phase velocity measurement is able to distinguish between the baseline and heat-damage conditions.

Figure 9:
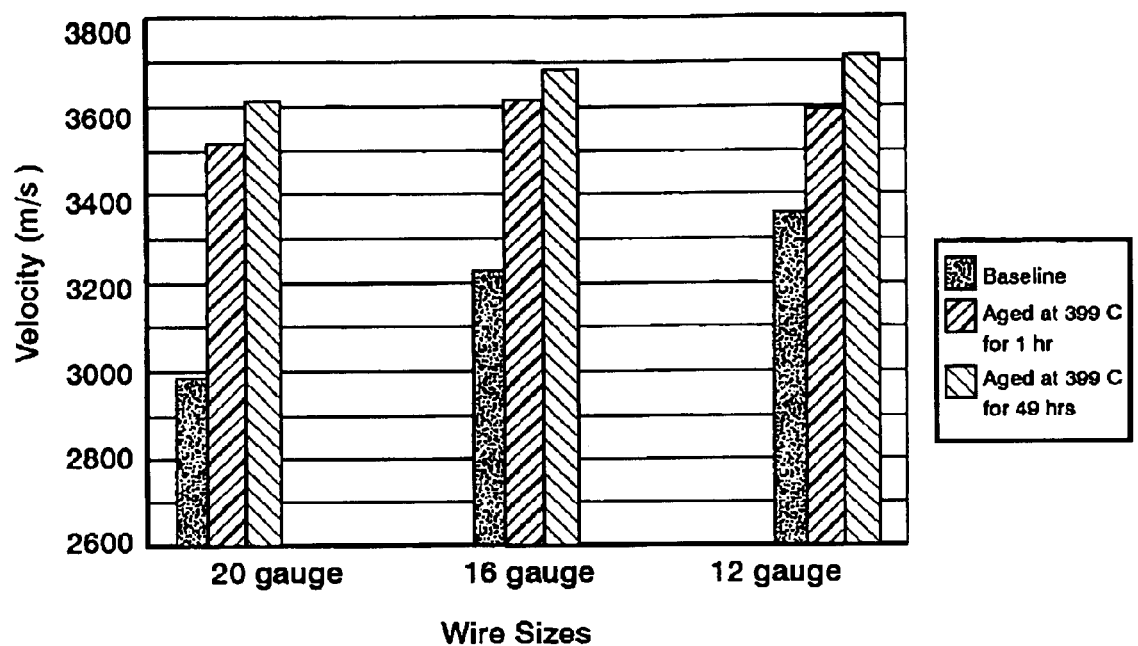
FIG. 9 shows experimental results for MIL-W-81381 wire.

In the experimental example shown in FIG. 7 and TABLE III, 12, 16 and 20 gauge MIL-W-81381 wire samples were heat-damaged. The insulation type on these samples was polyimide/FEP laminated tapes. FIG. 9 shows the results for each of the gauge wires at the baseline condition, after heating at 399 degrees C for one hour and after heating at 399 degrees C for 49 hours.

TABLE III

|  | Gauge | | |
| --- | --- | --- | --- |
|  | 12 | 16 | 20 |
| Mil spec variant | /12 | /21 | /7 |
| Overall Dia. (mm) | 2.50 | 1.63 | 1.29 |
| Wire Bundle Dia. (mm) | 2.09 | 1.33 | 0.94 |
| Insulation Thk. (mm) | 0.21 | 0.15 | 0.17 |
| Wire Strands per Bundle | 37 | 19 | 19 |
| Wire Strand Gauge | 28 | 29 | 32 |
| Conductor Type | Ni coated copper | Sn coated copper | Ag coated copper |
| Max. Operating Temp. | 200° C. | 200° C. | 200° C. |

Figure 10:
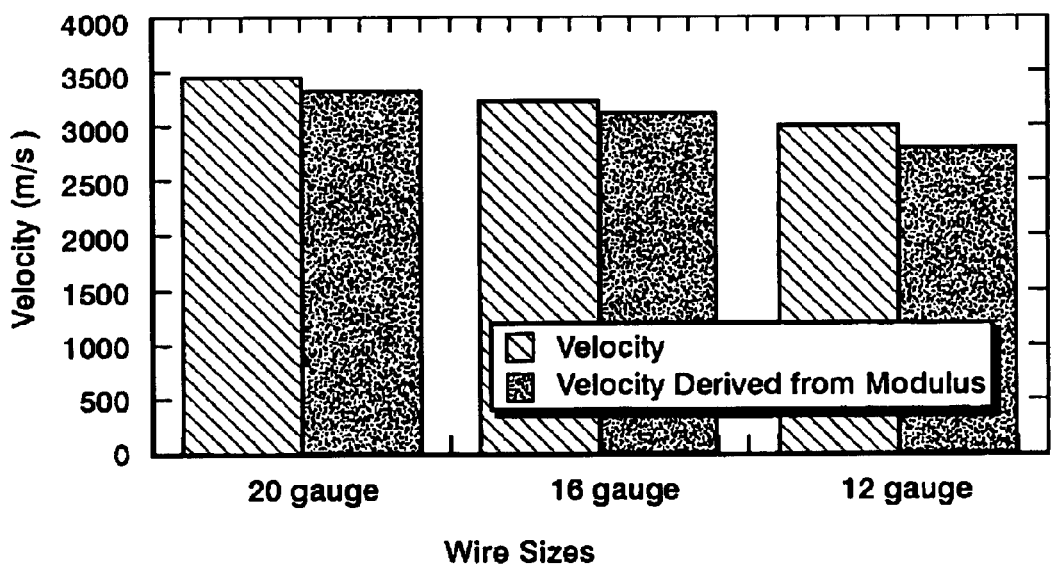
FIG. 10 shows baseline values of MIL-W-81381 velocity measurements compared to modulus-derived velocity.
Figure 11:
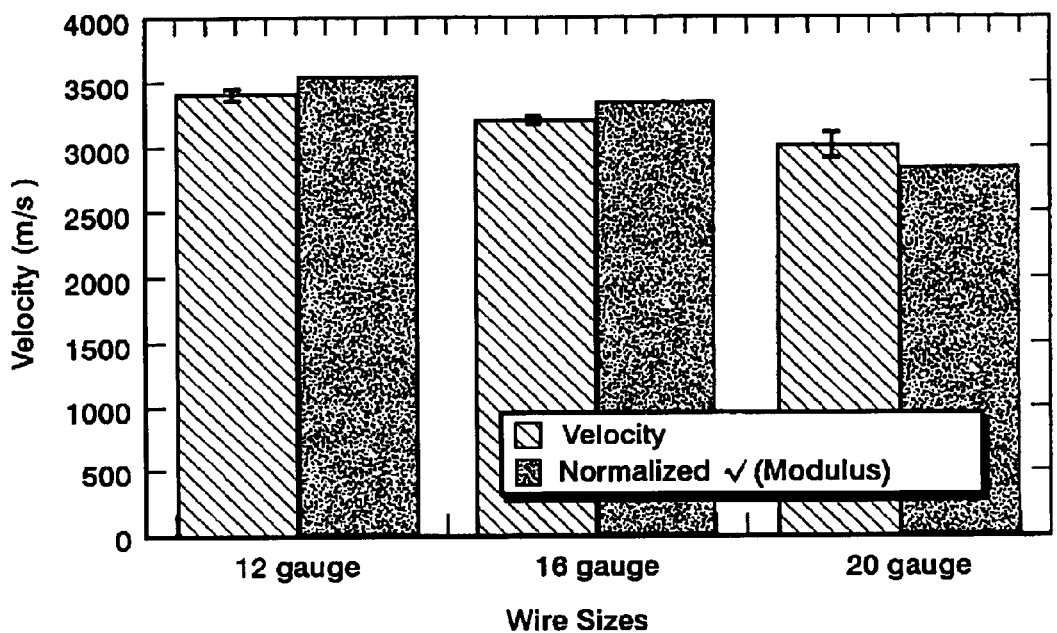
FIG. 11 shows baseline values of MIL-W-81381 velocity measurements compared to normalized modulus measurements.

Additional experimental examples were conducted to compare the ultrasonic damage measurement to the mechanically measured damage. For the mechanical measurement, a small table top electromechanical load frame was used, having a 1000 pound load cell, 1 inch extensometer, and load ranges of up to 100 pounds for 12 gauge wire and up to 40 pounds for 20 gauge wire. FIG. 10 shows the baseline values of MIL-W-81381 velocity measurements compared to the velocity derived from modulus measurements. FIG. 11 shows the baseline values of MIL-W-81381 velocity measurements compared to normalized modulus measurements. The ultrasonic guided wave velocity of the lowest order axisymmetric mode for 12 gauge wires were measured as 3352, 3596 and 3712 m/s for baseline, one hour and 49 hours at 399 degrees C, respectively. Mechanically, the tensile module of these wires were 8020, 10882 and 15894 ksi for baseline, one hour, and 49 hours at 399 degrees C, respectively.

Figure 12:
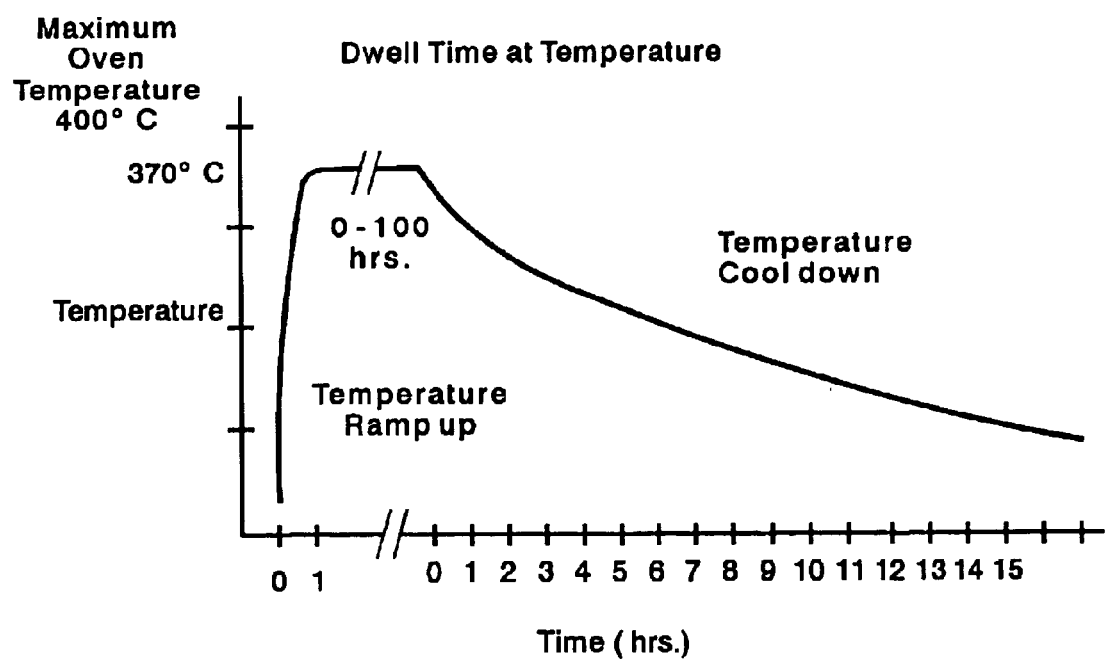
FIG. 12 illustrates a heat treatment profile.
Figure 13:
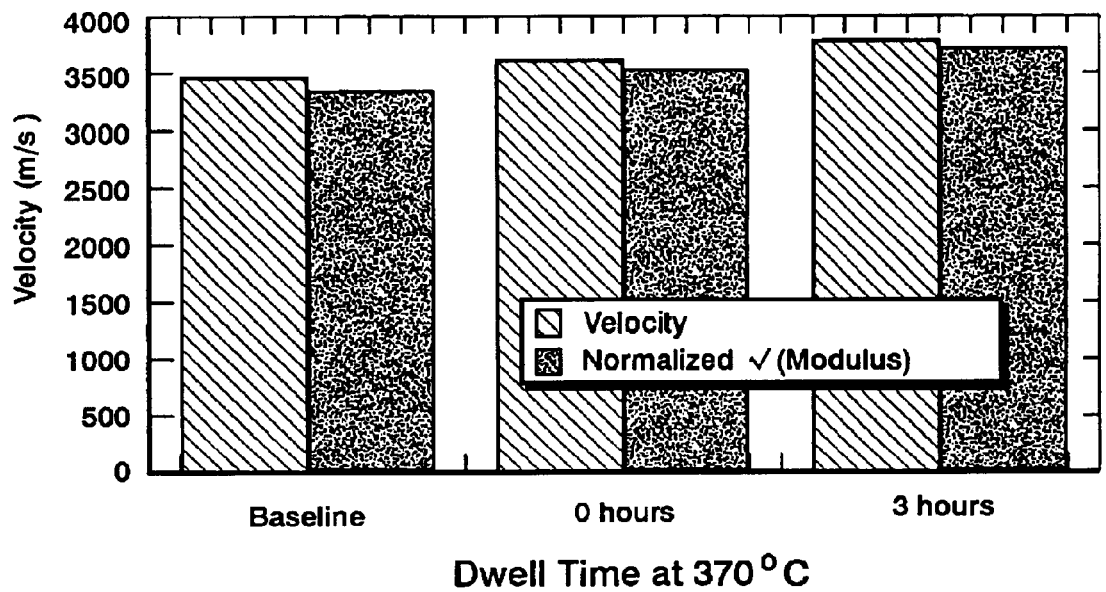
FIG. 13 shows velocity measurement for heat-damaged MIL-W-81381 wire compared to modulus-derived velocity using the heat treatment profile of FIG. 12.
Figure 14:
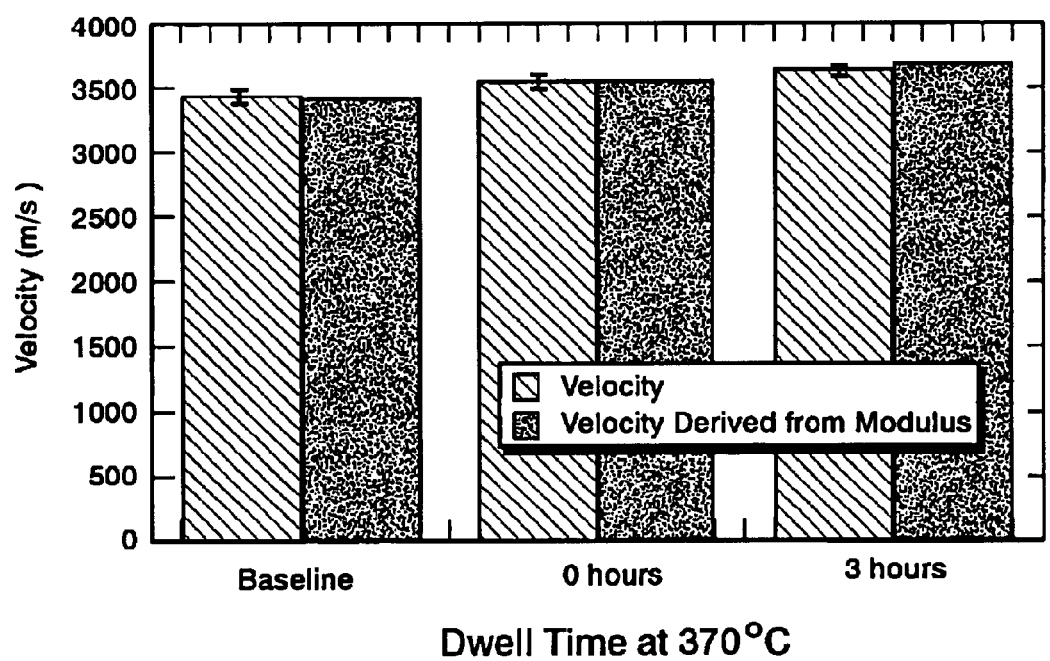
FIG. 14 shows velocity measurement for heat-damaged MIL-W-81381 wire compared to normalized modulus measurement using the heat treatment profile of FIG. 12.
Figure 15:
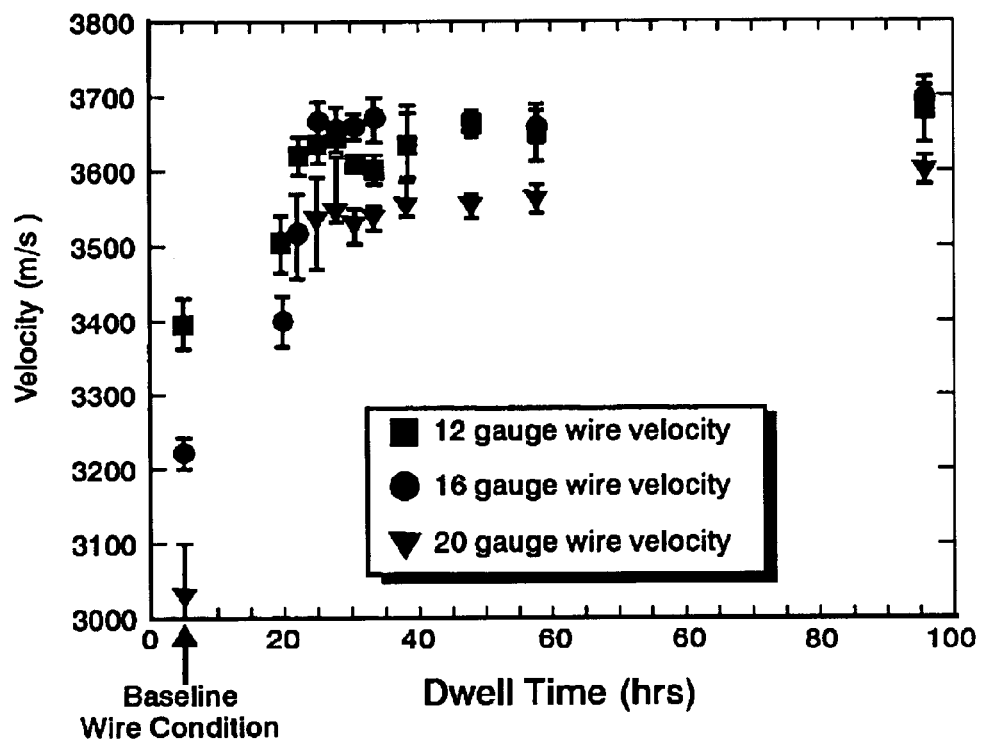
FIG. 15 shows axisymmetric phase velocity of Kapton® insulated wire.
Figure 16:
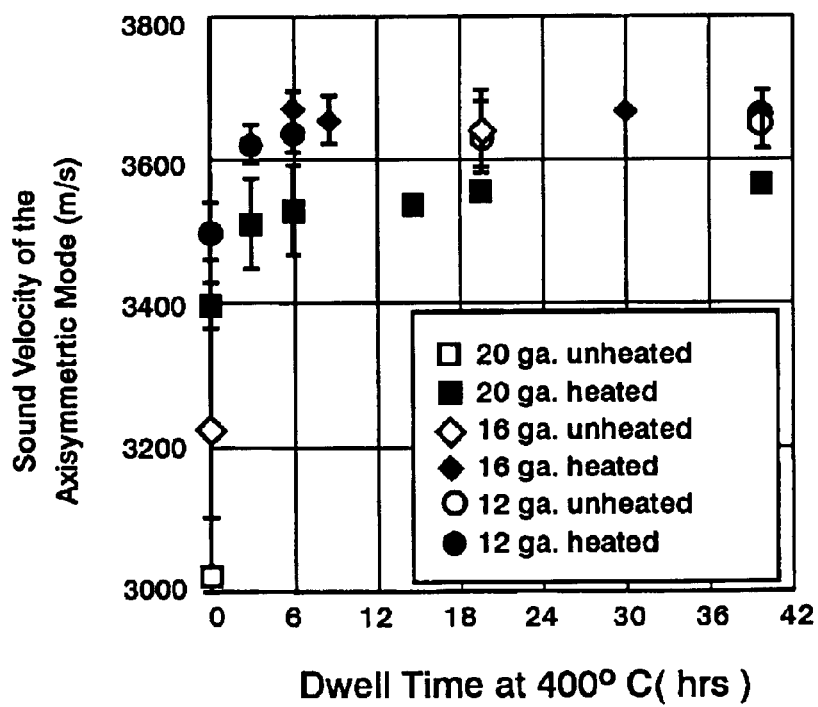
FIG. 16 shows axisymmetric phase velocity of aromatic polyimide insulated wire.

FIGS. 13 and 14 show additional results obtained for the MIL-W-81381 wire using the heat treatment profile shown in FIG. 12. The profile illustrates the temperature ramp up to 370 degrees C, the dwell at 370 degrees C, and the temperature cool down. FIGS. 15 and 16 show additional experimental results for Kapton® insulated wire at dwell temperature 370° C. and aromatic polyimide wire insulation at dwell temperature 400° C., respectively. The wire cores were stranded copper. For the 12 gauge, the copper was a nickel-coated wire, for the 16 gauge the copper was tin-coated wire, and for the 20 gauge wire, the copper was silver coated.

Figure 17:
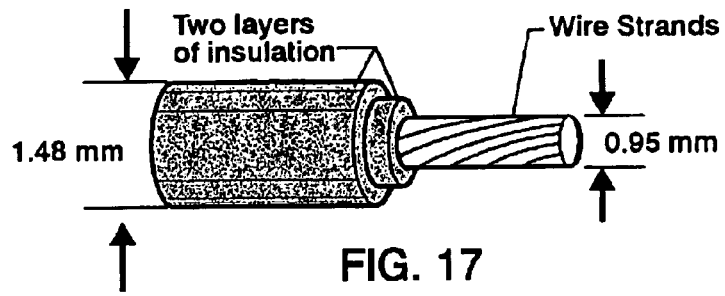
FIG. 17 shows a MIL-W-22759/34 AWG 20 wire sample.
Figure 18A:
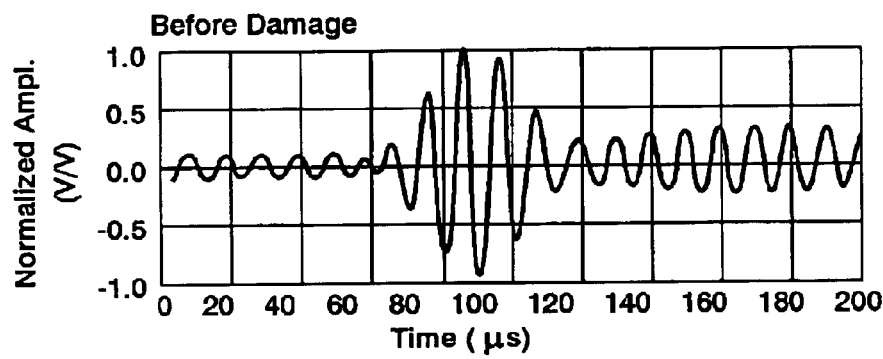
FIGS. 18A–18C illustrate experimental results for the MIL-W-22759/34 AWG 20 wire sample.
Figure 18B:
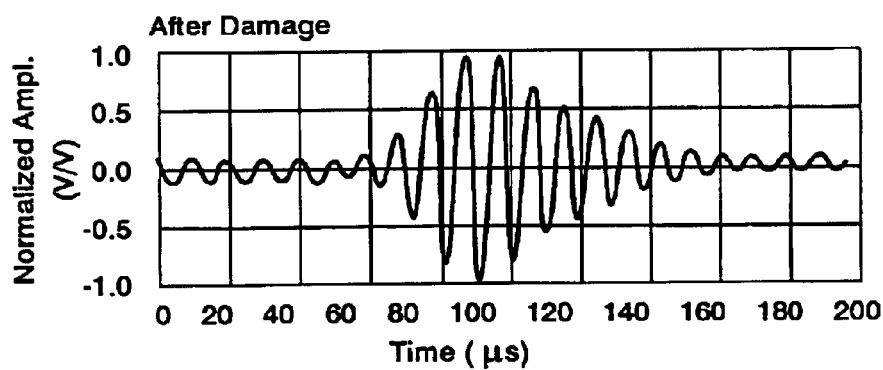
Figure 18C:
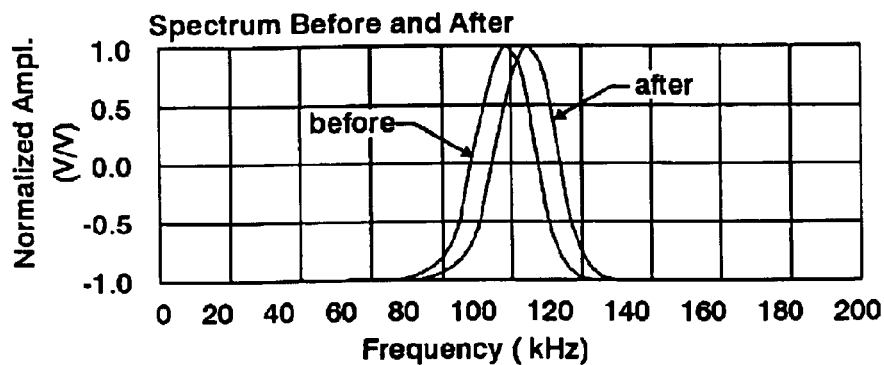

In addition to providing quantitative information concerning degradation of wire insulation, the present invention is also useful for detecting actual flaws in the insulation, such as a cut. A signal loss would be apparent using the pitch and catch method. Use of the pulse echo method would allow one to see a reflected signal from the flaw. FIGS. 18A through 18C are illustrative of the amplitude change resulting from a flaw such as a cut. More specifically, FIGS. 18A–18C show the results for the wire shown in FIG. 17 undamaged and damaged by a cut approximately 0.2 in. in length and extending through to the conductor. The experimental set-up illustrated in FIG. 1 with an input signal of a 100 kHz, 5 cycle Gaussian enveloped sine wave was used. The frequencies were determined in a manner similar to earlier discussions. The number of cycles was determined based on general knowledge. The wire had 19 strands, each approximately 0.2 mm in diameter, and two layers of insulation.

Figure 19:
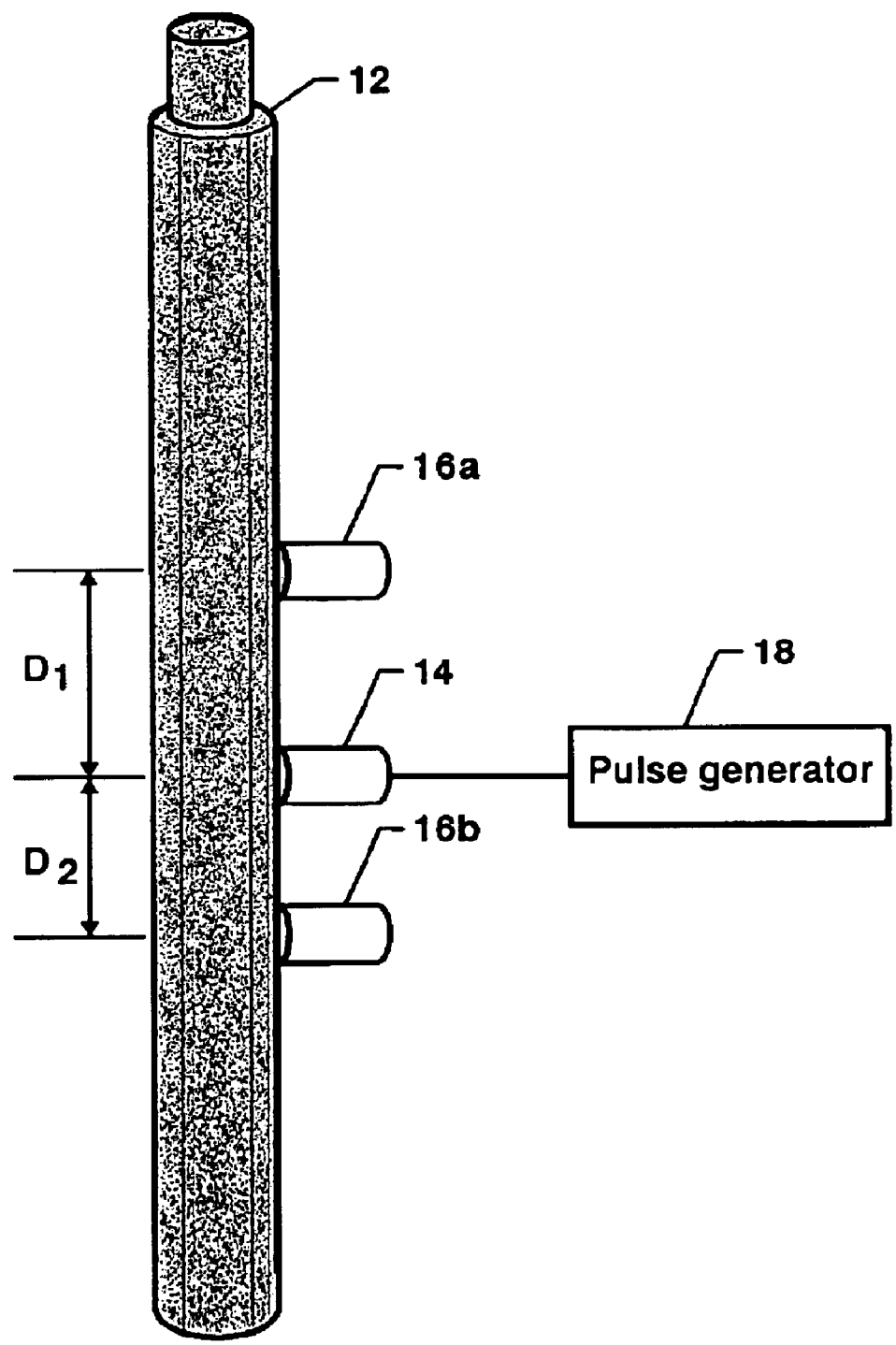
FIG. 19 is a schematic of an embodiment having one transmitter transducer and two receiver transducers.
Figure 20:
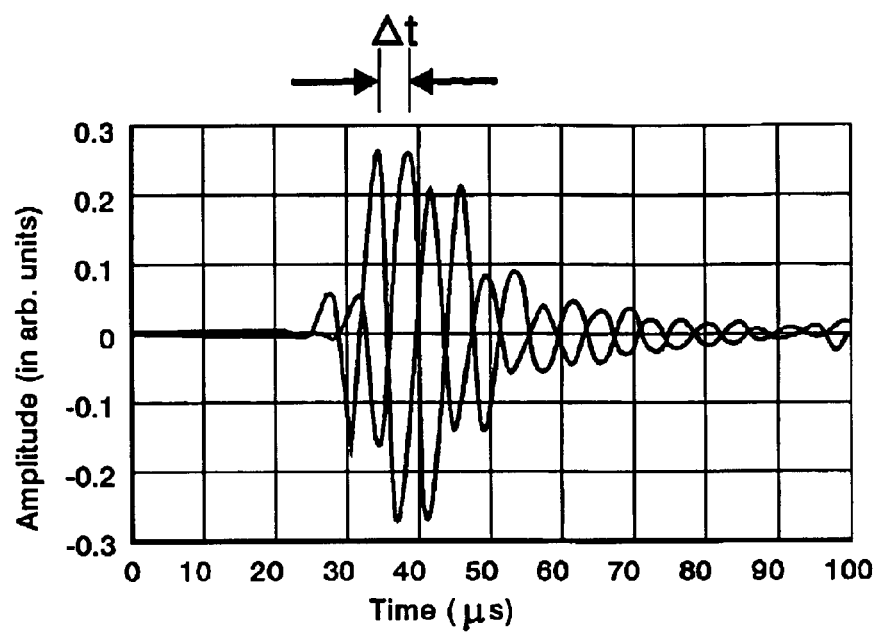
FIG. 20 illustrates the time difference between received signals for the embodiment shown in FIG. 19.

In an alternate embodiment, as shown in FIG. 19, three transducers are used, where the transmitter transducer 14 is located between two outer receiver transducers 16a and 16b. If the distances D1 and D2 are not equal, then the difference between the time of the received signals, as shown in FIG. 20, divided into the differences in transducer spacing will give the velocity $V=(D1-D2)/_\Delta t)$. This eliminates the need to move the receiver or transmitter transducer to obtain various measurements from which the wave velocity is calculated. Additional receivers can be used to try to improve accuracy. Also, this embodiment lends itself to a phase wave measurement technique. In the phase wave technique, either one transducer is used in a pulse echo manner with the distance to two well-defined reflection points that are known, or two transducers (one transmitting and one receiving) are needed for accurate velocity measurements. The phase wave measurement technique is discussed in more detail in Wolfgang Sachse and Yih-Hsing Pao, "On the Determination of Phase and Group Velocities of Dispersive Waves in Solids," *J. Appl. Phys.*, Vol. 49(8), pp 4320–4327, August 1978. The greater the spacing, the more accurate the velocity measurements. More than two receiver transducers can be used but each each measurement affects the signal, so that more transducers will measure a modified signal. To facilitate movement of the transducers, all three transducers can be clamped as a unit onto the wire.

In alternative embodiments, either the transmitter transducers or the one or more receiver transducers may be angled at other than 90 degrees to the wire. The angling of the transmission transducers produce surface waves instead of body waves. In this embodiment, although the signal may be small due to less efficiency in generating the signal, detection efficiencies are improved since the wave spends most of its time in the insulating material and more efficiently interacts with a flaw. Angling of the receiver transducers might be beneficial in evaluating damage such as cracks and surface damage to the insulation.

In another alternate embodiment, the ultrasonic waves are laser generated. The laser generation allows for non-contacting measurements to be made at a distance. The heat created by the laser causes a deformation in the cable insulation, which generates a detectable acoustic signal. The laser may be a low-power laser diode or a Q-switched laser. In general, Q-switched lasers are used for ultrasonic wave generation. For the purpose of the lower frequencies, the modulated laser diode may generate lower frequencies better. The use of a laser diode to generate ultrasound is attractive because of its low cost, small size, lightweight, simple optics and modulation capability. The laser diode generates via a coded low power signal so that little or no damage to the wire insulation occurs. Using cross correlation techniques, the ultrasonic signal can be recovered. Cross correlation techniques are known in the art and are described in numerous publications such as Cook, C. E., M. Bernfeld, and C. A. Palmieri, "Matched Filtering, Pulse Compression and Waveform Design," Radars, Volume 3: Pulse Compression, edited by D. K. Barton, Artech House, Massachusetts, 1975; and Furgason, E. S., V. L. Newhouse, N. M. Bilgutay, and G. R. Cooper, "Application of Random Signal Correlation Techniques to Ultrasonic Flaw Detection," Ultrasonics, January 1975. Laser detection can also be utilized. A discussion of laser detection in general can be found at C. B. Scruby and L. E. Drain "Laser Ultrasonics, Techniques and Applications," Adam Hilfer, N.Y., 1990. These laser generation and/or detection embodiments would be desirable in an area where a non-contacting measurement is desired, such as in an area that is more remote and difficult to reach. The use of a Q-switched laser (high frequency) versus a laser diode (low frequency) is based on the frequency desired.

Figure 21:
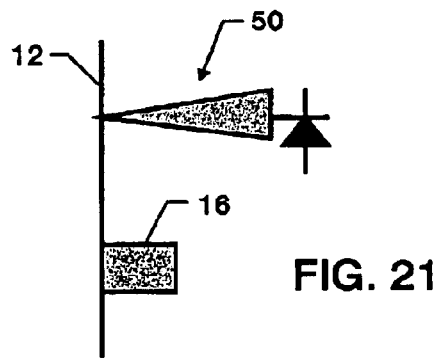
FIG. 21 is a schematic of an embodiment utilizing a laser diode for signal generation.
Figure 22:
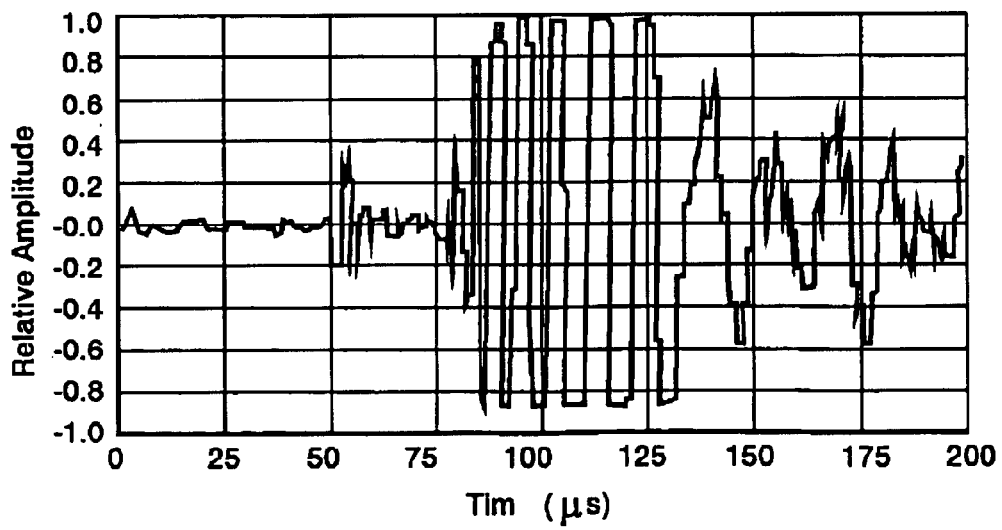
FIG. 22 shows typical experimental results obtained using laser-diode signal generation.
Figure 23A:
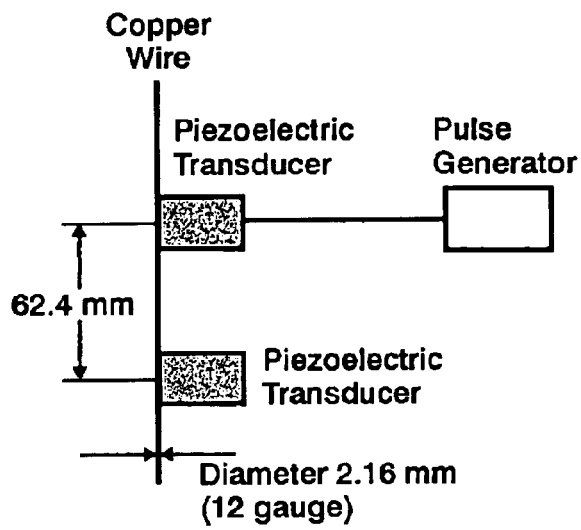
FIGS. 23A–23C illustrate the experimental set-up and results for a pulsed piezoelectric transducer and a modulated piezoelectric transducer.
Figure 23B:
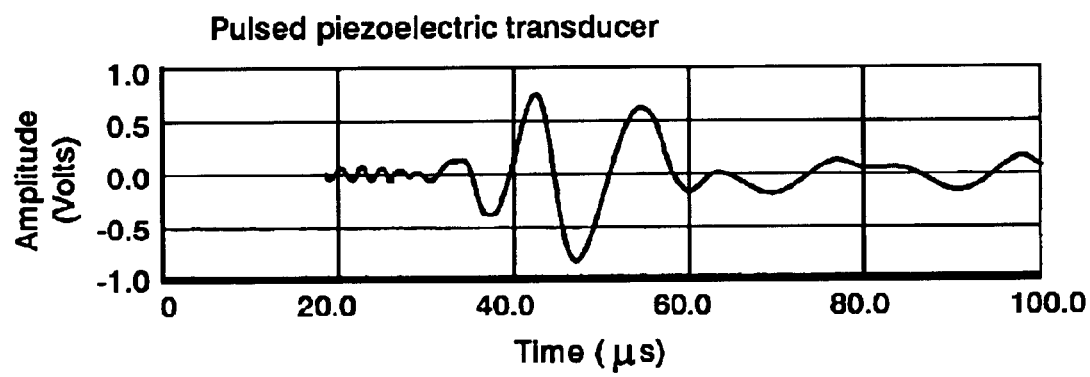
Figure 23C:
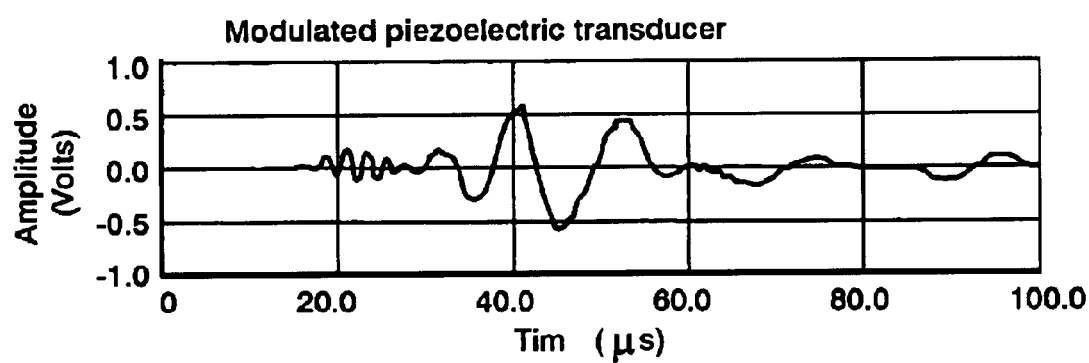
Figure 24A:
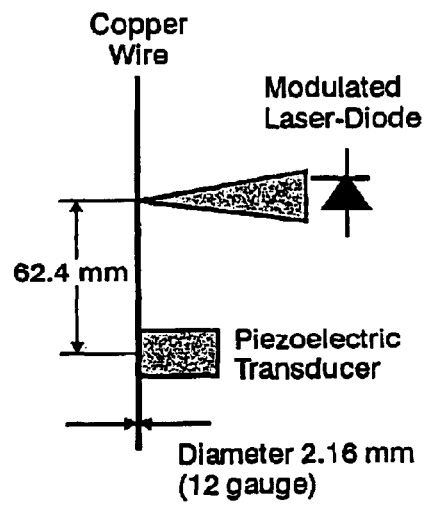
FIGS. 24A–24B illustrate experimental set-up and results obtained using a modulated laser diode.
Figure 24B:
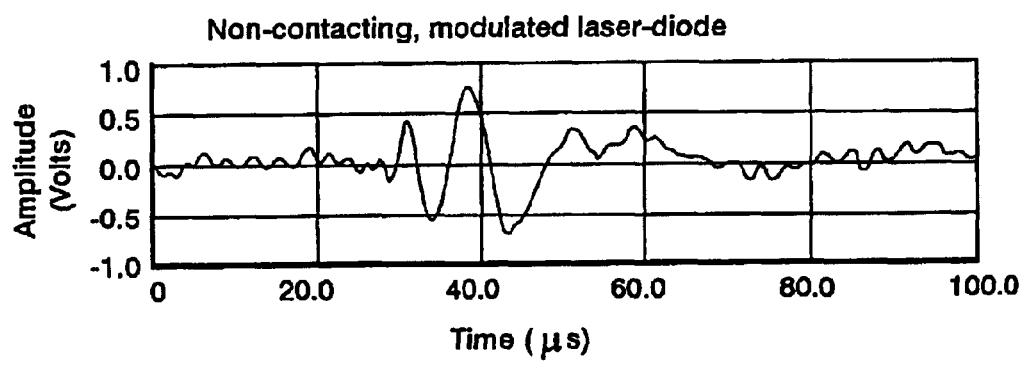

In an experimental example, having the set-up shown in FIG. 21, a 150 mW modulated laser diode 50 was used to generate ultrasound and a conventional piezoelectric transducer 16 was used as the receiver. Generally, the highest power that will not damage the material should be used. A conventional ultrasonic signal was recovered by signal correlation. The laser-diode beam incident on the wire insulation was 2 mm in diameter and had a power density of 17.83 mW/mm2. The power was measured with a calibrated power detector. A frequency generator modulated the laser diode drive current and the beam intensity in a frequency swept pattern from 1 kHz to 100 kHz. The insulation became damaged (slightly blackened) when the power density reached 20 mW/mm2. The previously discussed 12-gauge MIL-W-22759/34 baseline sample and the 12 gauge sample that was heat damaged at 349 degrees C for one hour were examined. A typical ultrasonic signal recovered from correlating the transmitted and received signals is shown in FIG. 22. The first flexural mode can be seen initiating at about 12 $\mu$s. The phase velocity of this flexural mode was measured by taking a series of measurements of a constant phase point as a function of generation point and receiver separation. The laser diode 50 was translated in millimeter increments while the piezoelectric ultrasonic receiver transmitter 16 was held in a fixed position. The phase point in time was plotted against the translation stage displacement and a linear curve fit was applied. The slope of the linear fit represents the flexural phase velocity. The baseline flexural phase velocity was 529 m/s while the heat-damaged sample had a phase velocity of 548 m/s. The flexural mode phase velocity measured with the laser is much lower than the axisymmetric mode phase velocity measured with the transducers. This is consistent with dispersion curve relations for cylindrical rods. These relations show the flexural mode phase velocity approaches zero as frequency approaches zero while the axisymmetric mode phase approaches the bar velocity as frequency approaches zero. Laser generation tends to generate very little of the axisymmetric mode, whereas the transducers tend to produce some axisymmetric mode, and because it arrives early, it is easy to isolate and measure. FIGS. 23 and 24 illustrate a comparison between pulsed piezoelectric transducer, modulated piezoelectric transducer and modulated laser diode generated ultrasound in a solid copper wire without insulation. FIGS. 23B and 23C show results obtained using pulsed and modulated piezoelectric transducers using the set-up shown in FIG. 23A. As shown, the two methods produce the same general signal. FIG. 24B shows results obtained using a modulated laser diode using the set-up shown in FIG. 24A.

Figure 25:
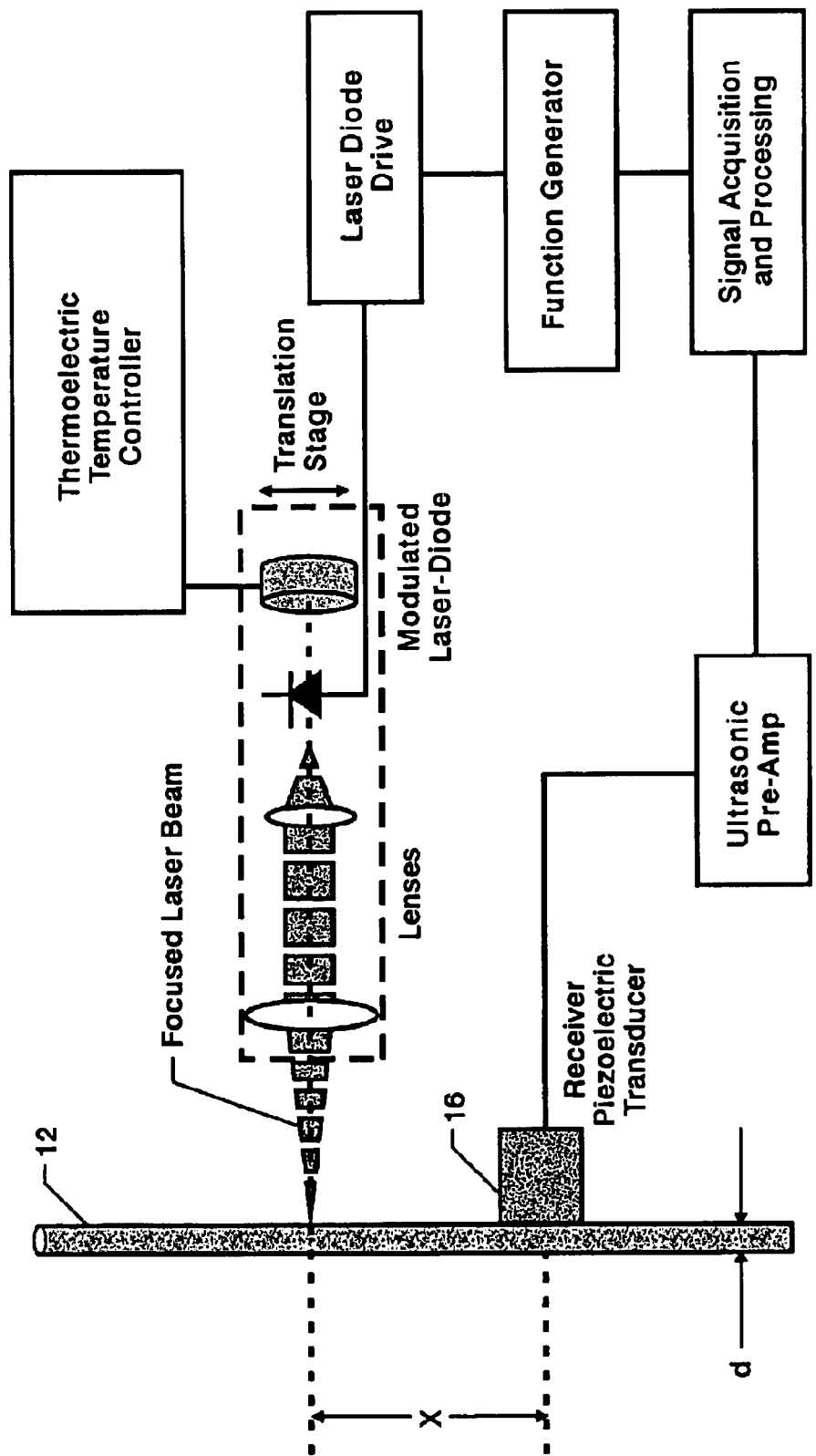
FIG. 25 shows a detailed schematic of an embodiment utilizing a laser diode.

FIG. 25 illustrates a more detailed schematic of an embodiment utilizing a laser diode for ultrasound generation. The Function Generator generates a swept frequency tone burst. A suitable Function Generator is a LeCroy Arbitrary waveform generator. That signal is used to drive the laser diode driver which controls the laser diode. A commercially available high-speed laser amplifier is suitable for the driver. The output from the modulated laser diode may be focused by one or more lenses to focus the incident beam. This focusing should produce a beam generally on the order of a few tens of microns in diameter. A thermoelectric temperature controller can be used to provide maximum stability to the laser diode and prevent mode hopping. The controller can also be helpful in extending the lifetime of the laser diode by operating at lower junction temperatures. The incident beam transmits an acoustic wave into the wire, which is received at piezoelectric receiver transducer 16. As discussed earlier, this embodiment is not limited to a single receiver transducer. The received signal is amplified prior to processing. Suitable for signal acquisition is a LeCroy digitizing oscilloscope which has signal processing capabilities to capture the signals and internal processing capabilities to perform cross correlation.

Figure 26A:
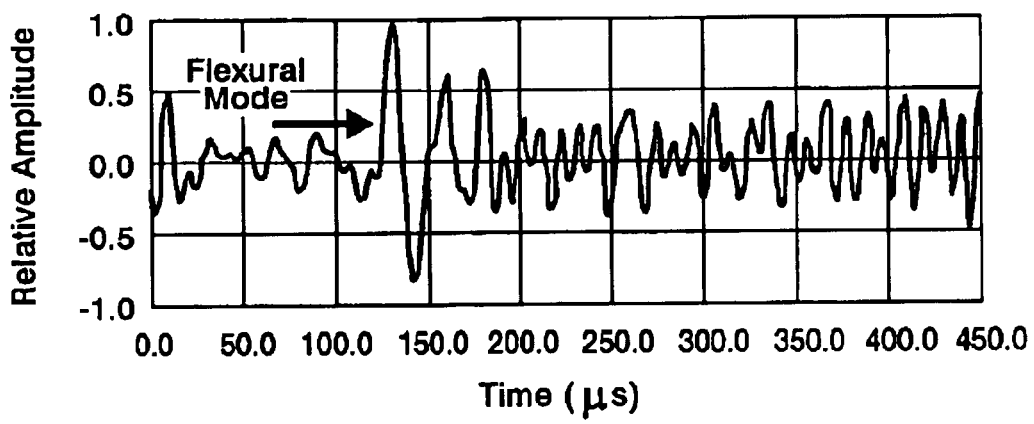
FIG. 26 shows experimental results for laser-diode generation in MIL-W-22759/34 wire.
Figure 26B:
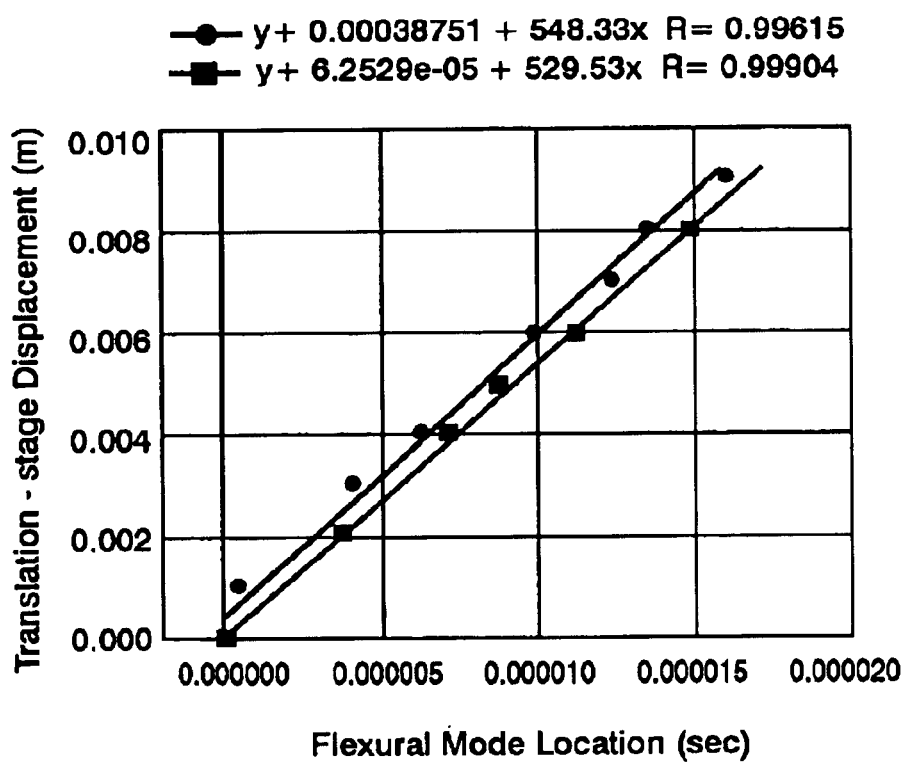

FIGS. 26A and 26B illustrate experimental data for 12 gauge MIL-W-22759/34 wire. The laser diode beam diameter was 2 mm, the power was 17.83 mW/mm2 and the modulation was 1 kHz to 100 kHz. The wire was heat damaged for one hour at 349 degrees C. The flexural mode phase velocity was determined to be 529 m/s and 548 m/s for the baseline and heat damages samples, respectively. This increase in velocity for the heat-damaged sample is consistent with the axisymmetric wave measurements made using piezoelectric transducers. The "translation stage" was a small manually operated motion controller that allowed the sample to be translated a small distance.

The present invention can be used for any layered media, including cylindrical or rectangularly shaped structures, and including media that is not conductive. In addition to the evaluation of insulation, it can also be used for evaluating coatings, as well as the conductor itself. It can also be used to evaluate stranded wire. The system is adapted, frequency for example, to measure the particular constituent condition. The stiffness of various layers would determine the ultimate efficacy of any testing. At the lowest frequencies, it would test the whole structure, but at higher frequencies, it would tend to test the layers with the lowest stiffness.

Additional discussion and experimental examples can be found in Robert F. Anastasi and Eric I. Madaras, Investigating the Use of Ultrasonic Guided Waves for Aging Wire Insulation Assessment, SPIE's 7th *Annual International Symposium on NDE for Health Monitoring and Diagnostics*, San Diego, Calif., Mar. 17–21, 2002; and Eric I. Madaras and Robert F. Anastasi, Investigating the Use of Ultrasound for Evaluating Aging Wiring Insulation, *5th Joint NASA/FAA/DoD Conference on Aging Aircraft*, Orlando, Fla., Sep. 10–13, 2001; and Robert F. Anastasi and Eric I. Madaras, Ultrasonic Guided Waves for Aging Wire Insulation Assessment, 28th *Annual Review of Progress in Quantitative Nondestructive Evaluation* (QNDE), Brunswick, Me., Jul. 29-Aug. 3, 2001, all herein incorporated by reference.

Although our invention has been illustrated and described with reference to the preferred embodiments thereof, we wish to have it understood that it is in no way limited to the details of such embodiment, but is capable of numerous modifications for many mechanisms, and is capable of numerous modifications within the scope of the appended claims.

What is claimed as new and desired to be secured by Letters Patent of the United States is:

1. A method for evaluating wire having more than one layer, comprising:
    transmitting a guided ultrasonic wave into the wire at a first location;
    receiving the guided ultrasonic wave at one or more one predetermined locations along the wire; processing the received guided ultrasonic wave to evaluate the wire.

2. The method of claim 1, wherein the wire is electrical wire.

3. The method of claim 1, wherein the wire comprises an insulated conductor.

4. The method of claim 3, wherein the processing step comprises evaluation of the insulation.

5. The method of claim 3, wherein the processing step comprises evaluation of the conductor.

6. The method of claim 3, wherein the processing step comprises evaluation of the insulation and the conductor.

7. The method of claim 1, wherein the wire is coated.

8. The method of claim 1, wherein the wire is stranded.

9. The method of claim 1, wherein the ultrasonic wave is a surface wave.

10. The method of claim 9, wherein the transmitter transducer is angled at other than 90 degrees to the wire.

11. The method of claim 1, wherein the ultrasonic wave is a body wave.

12. The method of claim 1, wherein the ultrasonic wave is transmitted by a transducer.

13. The method of claim 1, wherein the transducer is clamped to the wire.

14. The method of claim 12, wherein the transducer is a piezoelectric transducer.

15. The method of claim 1, wherein the ultrasonic wave is transmitted by a laser.

16. The method of claim 15, wherein the laser is a Q-switched laser.

17. The method of claim 15, wherein the laser is a laser diode.

18. The method of claim 1, wherein the ultrasonic wave is received by one or more transducers.

19. The method of claim 18, wherein the receiver transducers are angled at other than 90 degrees to the wire.

20. The method of claim 18, wherein the one or more transducers are piezoelectric transducers.

21. The method of claim 1, wherein the ultrasonic wave is received by a laser.

22. The method of claim 1, wherein the ultrasonic wave is received at the same location as it is transmitted.

23. The method of claim 1, wherein the ultrasonic wave is received at one or more locations separate from the location of generation.

24. The method of claim 1, wherein the step of processing the received wave comprises the step of calculating the phase velocity of the wave.

25. The method of claim 1, wherein:
    the step of transmitting the ultrasonic wave comprises transmitting the wave at a predetermined angle with respect to the wire; and
    the step of receiving the ultrasonic wave comprises receiving the wave at an angle with respect to the wire that is substantially the same as the predetermined angle.

26. The method of claim 1, wherein:
    the step of transmitting the ultrasonic wave comprises transmitting the wave at a predetermined angle with respect to the wire; and
    the step of receiving the ultrasonic wave comprises receiving the wave at an angle with respect to the wire that is different than the predetermined angle.

27. The method of claim 1 further comprising the step of generating a pulse, and wherein the transmitting step further comprises the step of applying the pulse to the wire.

28. The method of claim 1 further comprising the step of generating a waveform, and wherein the transmitting step further comprises the step of applying the waveform to the wire.

29. The method of claim 1 wherein the receiving step comprises the step of converting the received wave into an electrical waveform.

30. The method of claim 1 wherein the step of processing comprises evaluation of the phase velocity of the received wave.

31. The method of claim 1 wherein the step of processing comprises evaluation of the waveform of the received wave.

32. The method of claim 1, wherein the step of processing further comprises comparison of the received wave to a pre-defined look-up table of baseline properties for the wire.

33. The method of claim 1, wherein the step of processing further comprises comparison of the received ultrasonic wave velocity properties to a predefined look-up table of baseline velocity properties for the wire.

34. The method of claim 1, wherein the step of processing further comprises comparison of the received ultrasonic wave attenuation properties to a predefined look-up table of baseline attenuation properties for the wire.

35. An apparatus for evaluating wire having more than one layer, comprising:
    a transmitting device for generating a guided ultrasonic wave into the wire at a first location;
    one or more receiving devices for receiving the guided ultrasonic wave at one or more predetermined locations along the wire;
    a processing device for processing the received guided ultrasonic wave to evaluate the wire.

36. The apparatus of claim 35, wherein the wire is electrical wire.

37. The apparatus of claim 35, wherein the wire comprises an insulated conductor.

38. The apparatus of claim 35, wherein the wire is coated.

39. The apparatus of claim 35, wherein the wire is stranded.

40. The apparatus of claim 35, wherein the processing step comprises evaluation of the insulation.

41. The apparatus of claim 35, wherein the processing step comprises evaluation of the conductor.

42. The apparatus of claim 35, wherein the processing step comprises evaluation of the insulation and the conductor.

43. The apparatus of claim 35, wherein the ultrasonic wave is a surface wave.

44. The apparatus of claim 35, wherein the ultrasonic wave is a body wave.

45. The apparatus of claim 35, wherein the transmitting device is an ultrasonic transducer.

46. The method of claim 45, wherein the transducer is angled at other than 90 degrees to the wire.

47. The apparatus of claim 35, wherein the transducer is clamped to the wire.

48. The apparatus of claim 35, wherein the transducer is a piezoelectric transducer.

49. The apparatus of claim 35, wherein the transmitting device is a laser.

50. The apparatus of claim 35, wherein the laser is a Q-switched laser.

51. The apparatus of claim 35, wherein the laser is a laser diode.

52. The apparatus of claim 35, wherein each receiving device is a transducer.

53. The apparatus of claim 52, wherein each transducer is a piezoelectric transducer.

54. The apparatus of claim 53, wherein each transducer is angled at other than 90 degrees to the wire.

55. The apparatus of claim 35, wherein each receiving device is a laser.

56. The apparatus of claim 35, wherein the ultrasonic wave is received at the same location as it is transmitted.

57. The apparatus of claim 35, wherein the ultrasonic wave is received at one or more locations separate from the location of transmission.

58. The apparatus of claim 35, wherein the processing device is a computer.

59. The apparatus of claim 35 further comprising a pulse generator.

60. The apparatus of claim 35 further comprising a waveform generator.

\* \* \* \* \*